United States Patent [19]
Markowitz

[11] 3,939,822
[45] Feb. 24, 1976

[54] DISPOSABLE BLOOD COLLECTION AND FILTERING DEVICE

[76] Inventor: Jack Markowitz, 3705 Fieldstone Road, Randallstown, Md. 21133

[22] Filed: Aug. 14, 1974

[21] Appl. No.: 497,284

[52] U.S. Cl. ............. 128/2 F; 128/272; 128/218 M
[51] Int. Cl.² ..................... A61B 19/00; A61B 5/14
[58] Field of Search ....... 128/2 F, 2 G, DIG. 5, 276, 128/278, 275, 272, DIG. 24, DIG. 28, 218 M, 220, 216, 218 D; 210/DIG. 23, DIG. 24, 477, 482

[56] References Cited
UNITED STATES PATENTS

| | | | |
|---|---|---|---|
| 2,176,042 | 10/1939 | Pittenger | 128/218 X |
| 2,518,165 | 8/1950 | Millard | 128/DIG. 5 |
| 2,609,818 | 9/1952 | Parrine | 128/216 |
| 2,769,444 | 11/1956 | Henderson | 128/216 |
| 2,908,555 | 10/1959 | Grosskopf | 128/272 X |
| 3,539,300 | 11/1970 | Stone | 23/253 |
| 3,596,652 | 8/1971 | Winkelman | 128/2 F |
| 3,654,925 | 4/1972 | Holderith | 128/272 |
| 3,701,434 | 10/1972 | Moore | 128/272 X |
| 3,706,305 | 12/1972 | Berger | 128/2 F |
| 3,750,645 | 8/1973 | Bennett et al. | 128/272 X |
| 3,753,432 | 8/1973 | Guerra | 128/2 F |

FOREIGN PATENTS OR APPLICATIONS

| | | | |
|---|---|---|---|
| 60,891 | 7/1954 | France | 128/2 F |

*Primary Examiner*—Aldrich F. Medberry
*Attorney, Agent, or Firm*—John F. McClellan, Sr.

[57] ABSTRACT

A blood collection and handling device having an elongate body comprising first and second evacuated test tubes connected by a coaxially disposed rubber conduit having a frangible valve in the bore, a compressible middle portion at the valve, and a filter in the bore; the first test tube connects to the rubber conduit proximate the valve and has an elastomeric end adapted for drawing blood into it by means of a double-ended needle, and the second test tube connects to the rubber conduit proximate the filter and has a rounded end.

3 Claims, 7 Drawing Figures

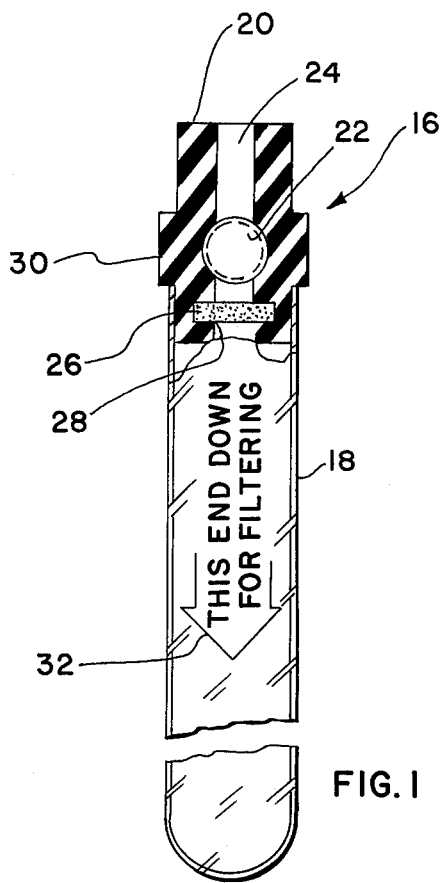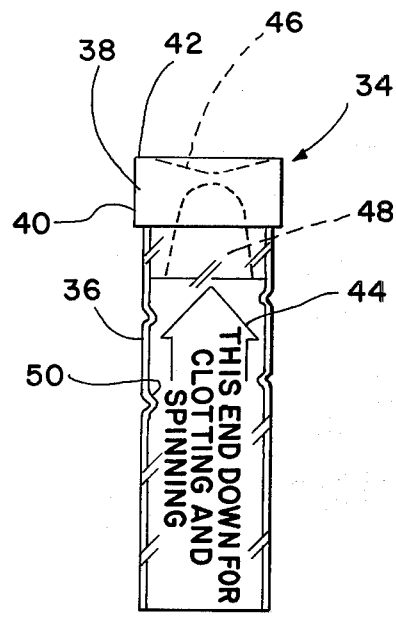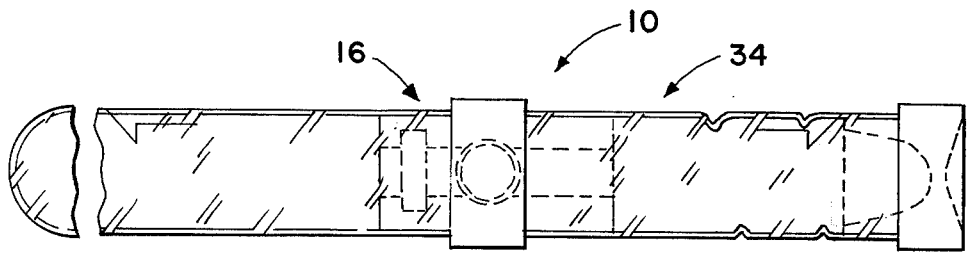

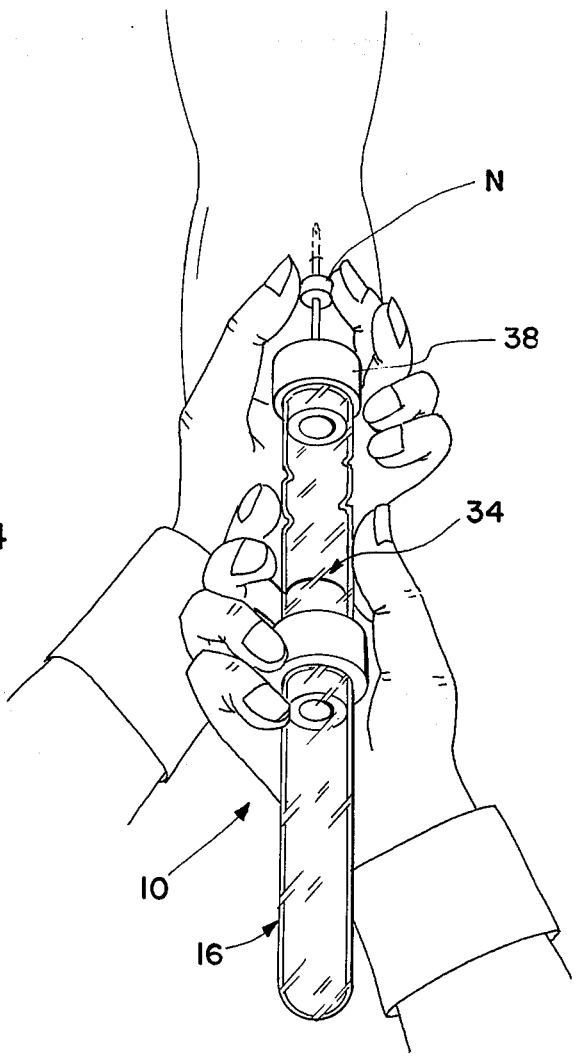
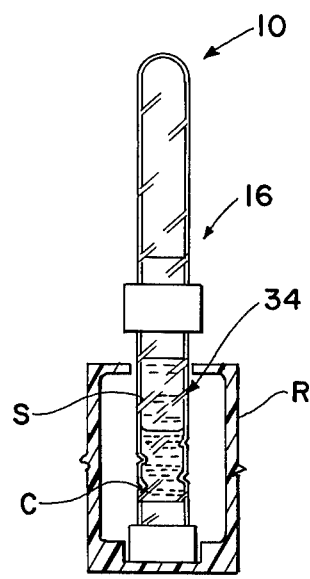
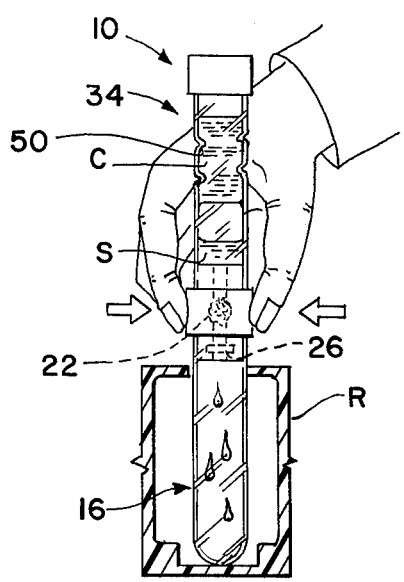
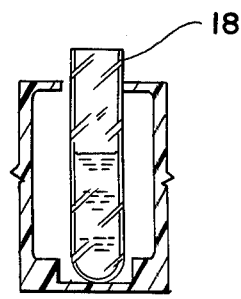
FIG. 4
FIG. 5   FIG. 6   FIG. 7

DISPOSABLE BLOOD COLLECTION AND FILTERING DEVICE

This invention relates generally to blood analysis and specifically to means and method for handling and separating components of blood.

Many syringe systems appear in the prior art, including these U.S. Pat. Nos. 3,753,432 issued Aug. 21, 1973, to L. A. Guerra, disclosing use of plural syringe chambers; 3,706,305 issued Dec. 18, 1972, to H. J. Berger et al, disclosing use of two double ended needles respectively supplying a first vacuum chamber and connecting to it a second vacuum chamber; 3,596,652 issued Aug. 31, 1971, to J. W. Winkelman, disclosing use of one form of ball valve between syringe chambers; and 3,539,300 issued Nov. 10, 1970, to E. W. Stone, disclosing first and second portions of a vacuum syringe chamber separated by a filter. Two foreign patents, French Pat. Nos. 968,833 and 60,891, disclose particular type ball valves in syringe structure.

However, the prior art devices fall short of achieving the objects of the present invention, a principal object of which is to provide an easily used disposable blood collection and handling system which simplifies, speeds and reduces error and cost in collecting and filtering biological sera.

Other objects are to provide a system as described which has an annular-end external configuration conducive of sanitary storage and induction of blood samples, which has no internal exposure to uncontrolled environments when assembled, which has frangible valve structure positively eliminating accidental re-use and affording optional modes of operation, which has differently contoured ends providing instant indication of proper orientation during stages of use, which has separately usable components, and which is outstandingly safe, secure and efficient in use.

In brief summary given for purposes of cursive description only, the invention includes plural separable vacuum chambers connectable through a frangible valve and filter and provided with means for introducing blood for separation thereby into components.

The above and other objects and advantages of the invenction will become more readily apparent from examination of the following description, including the Figures, in which like numerals designate like parts:

FIG. 1 is a plan view in partial section;

FIG. 2 is a plan view;

FIG. 3 is a plan view;

FIG. 4 is an isometric view; and

FIGS. 5, 6 and 7 are side elevations.

FIGS. 1, 2 and 3 illustrate respectively the two component subassembly units of the invention and the complete assembly.

Referring to FIG. 1, Unit 1, designated by reference numeral 16, consists of a standard test tube 18 of any chosen length, depending on volume of filtrate to be accumulated, a cylindrical rubber connector or resilient tubular conduit 20 tightly fitted in the test tube, a thinwall glass sphere 22 forcibly inserted in the coaxially disposed bore 24 of the conduit to act as a frangible valve, and a filter disc 26 held in a socket 28 in the connector transversely across the bore at the mouth of the test tube.

The conduit has a cylindrical flange 30 extending axially at the midportion in the region of the glass sphere, serving as a test tube locator stop and double seal, and as a safety flange during assembly of rubber into test tube. The unit is evacuated by any standard techniques, as by assembly in a vacuum, or through a needle.

Unit 1 is separately usable as a vacuum filter by supporting it in the vertical position indicated by markings 32, containing fluid to be filtered in the upper end as by means of a funnel stem fitted in the bore, and crushing the glass sphere by pinching the flange. Alternatively a test tube can be used in place of the funnel.

Referring to FIG. 2, separately usable test tube like Unit 2, designated by reference numeral 34, consists of a cylindrical glass tube 36 with a rubber closure 38 hermetically sealing one end.

A cylindrical flange 40 at one end of the closure serves as a stop, safety, and seal, and has an end face 42 square with the axis, which serves as a base on which to stand the unit (and the full assembly) as directed by markings 44 on the tube. A conical exterior recess 46 makes the base more stable on uneven surfaces by leaving a peripheral annulus, and more sanitary by recessing the center, through which blood is supplied through a needle, as will be described. An interior conical recess 48 in the closure provides flexibility and lessens the needle travel required for penetration.

The tube is dimpled adjacent the closure, providing interior protrusions 50 for retaining coagulated blood, as referred to in the next Figures.

Diameter of the tube, like that of the test tube of Unit 1, is such as to form a hermetic seal with the connector of Unit 1.

Referring to FIGS. 3–5, Units 1 and 2, (16 and 34) assemble to form the complete embodiment 10 of the present invention, both units being preliminarily evacuated to a predetermined degree, depending on pumping capacity desired for the particular application.

FIG. 4 shows the first step in using the assembly; a double-ended needle N of any suitable conventional design is inserted into the blood vessel at one end and then through the center of the rubber closure 38, thus drawing a determinable quantity of blood into Unit 2 (34), which in this context, is a first chamber, Unit 1 being the second chamber to receive fluid.

In the next step, FIG. 5, the assembly is rested on the base or annulus of the rubber closure, in accordance with the arrow and legend on the side of Unit 2, to separate into clotted portion C and serum S. It may be centrifuged in this position if desired for any special reason. A conventional rack R is employed to guard against tipping over during the waiting interval.

Next, FIG. 6, the assembly is inverted in accordance with the arrow and legend on Unit 1 (16). The clotted portion C is held by the interior protrusion 50, with the serum S below, in this position. The sphere 22 is then crushed by manual pressure on the sides of the elastic conduit (arrows) causing the serum to be drawn down through the filter 26 into Unit 1 (16). The sphere is of very thin wall construction, in the region of a few thousands of an inch thick, so that a light pinch in the region crushes it.

Finally, FIG. 7, the test tube 18 containing the filtered serum to be analyzed is separated and the upper portions of the unit are discarded.

From the foregoing it will be apparent that this invention realizes the numerous objects set out and more.

Efficiency of design permitting rapid use and economical discard appear throughout.

The need to centrifuge is eliminated in most applications. The frangibility of the spherical valve prevents accidental re-use of the filter, since the user immediately feels the lack of resistance when squeezing the elastic conduit. The static design eliminates plungers and internal sliding operations, and provides the positive sealing of oversize glass sphere in smooth wall elastic conduit. The general design affords wide interchangeability tolerances through the use of elastic-to-rigid connections throughout. Retention of clotted material by integral deformations in the glass tubular portions (the glass parts may be of any suitable plastic) avoids the need for additional filter structure to prevent clogging the filter with the clotted portion. The glass fragments themselves comprise a coarse filter bed. The filter disk itself, which may be of any conventional rigid or semi-rigid material and porosity, is easily inserted during manufacture and is additionally retained and sealed by compression of the elastic conduit on insertion in the test tube portion. The different configurations of the two ends and the directive markings doubly insure correct orientation and quick visual and tactile checking of large numbers on the devices during the successive steps of use, and the coaxial relation of the parts provides for easy, secure handling without surprises, and for uniformity of observation.

Finally, it will be appreciated that the hollow glass sphere itself is a capacious container as well as a valve, and can contain preservative or other substance to be released immediately prior to filtration, or can be gas filled or evacuated, for coaction with the serum, and also with the filtration process.

Obviously many modifications and variations of the present invention are possible in light of the above teachings. For example, the spherical shape of the valve member could be elliptical and so of greater capacity even though the uniformity of the sphere is greater, and the entire member could be of some solid, easily frangible material. It is, therefore, to be understood that within the scope of the appended claims the invention may be practiced otherwise than as specifically described.

What is claimed and desired to be protected by United States Letters Patent is:

1. In a blood handling system having first and second evacuated chambers, means for affixing the chambers together detachably, means for admitting fluid into the first chamber including a resilient closure at one end thereof, means for valving fluid from the first chamber to the second chamber, and means for separating components of the fluid, the improvement comprising: the means for affixing comprising a resilient tubular conduit having a first end resiliently fitted into the first evacuated chamber, a second end resiliently fitted into the second evacuated chamber, a middle portion larger in diameter than said first and second ends spacing-apart the ends of said first and second evacuated chambers a distance permitting said middle portion to be manually squeezed inward between the ends of the first and second evacuated chambers; means for valving, comprising a spherical member of frangible material resiliently fitted in sealing contact within the bore of the resilient tubular conduit in said middle portion between the ends of said first and second evacuated chambers in position to be crushed by a said manual squeeze; and a filter resiliently fitted in the bore within said second end of the resilient tubular conduit inserted in said second evacuated chamber, with the end of said second evacuated chamber positioned for retaining the filter against disturbance by a said manual squeezing to crush the frangible member.

2. In a blood handling system as recited in claim 1, the means for separating components of the fluid including a plurality of dimple-like contours forming a plurality of interior protrusions in the first chamber for retaining coagulated blood.

3. In a blood handling system as recited in claim 1, said evacuated chambers having directional indication thereon, a first directional indication indicating that the first evacuated chamber be oriented downwardly for clotting and spinning and a second directional indication indicating that the second evacuated chamber should be oriented downwardly for filtering.

* * * * *